(12) United States Patent
Block et al.

(10) Patent No.: US 6,213,120 B1
(45) Date of Patent: Apr. 10, 2001

(54) DEVICE AND METHOD FOR DETERMINING GAS VOLUME AND VOLUMETRIC CHANGES IN A VENTILATOR

(75) Inventors: Frank E. Block, Little Rock, AR (US); Gustaf Järnefelt, Helsinki (FI)

(73) Assignee: Instrumentarium Corporation, Helsinki (FI)

( * ) Notice: Subject to any disclaimer, the term of this patent is extended or adjusted under 35 U.S.C. 154(b) by 0 days.

(21) Appl. No.: 08/916,062

(22) Filed: Aug. 21, 1997

(51) Int. Cl.$^7$ .................................................. A61M 16/00
(52) U.S. Cl. ............................ 128/204.23; 128/204.21; 128/205.13; 128/205.23
(58) Field of Search .................... 128/203.28, 204.19, 128/204.23, 204.28, 205.14, 205.16, 205.17, 205.18, 205.23, 204.21, 205.13

(56) References Cited

U.S. PATENT DOCUMENTS

| | | |
|---|---|---|
| 4,127,121 | 11/1978 | Westenskow et al. . |
| 4,262,667 * | 4/1981 | Grant .............................. 128/204.21 |
| 4,340,044 * | 7/1982 | Levy et al. ....................... 128/204.21 |
| 4,354,984 | 10/1982 | Richardson et al. . |
| 4,432,238 * | 2/1984 | Tward .................................... 73/724 |
| 4,493,614 | 1/1985 | Chu et al. . |
| 4,905,685 * | 3/1990 | Olsson et al. .................... 128/204.21 |
| 5,056,513 | 10/1991 | Boutin . |
| 5,317,918 * | 6/1994 | Lew ..................................... 73/718 |
| 5,322,058 * | 6/1994 | Pasternack ....................... 128/204.28 |
| 5,490,499 * | 2/1996 | Heinonen et al. ............... 128/203.28 |
| 5,509,406 | 4/1996 | Kock et al. . |
| 5,647,352 | 7/1997 | Niemi et al. . |
| 5,678,540 * | 10/1997 | Kock et al. ...................... 128/205.13 |
| 5,857,458 * | 1/1999 | Tham et al. ...................... 128/203.12 |
| 5,979,443 * | 11/1999 | Dingley ............................. 128/204.28 |

FOREIGN PATENT DOCUMENTS

| | | |
|---|---|---|
| 81/02677 | 10/1981 | (WO) . |
| 93/00952 | 1/1993 | (WO) . |

* cited by examiner

Primary Examiner—John G. Weiss
Assistant Examiner—V. Srivastava
(74) Attorney, Agent, or Firm—Andrus, Sceales, Starke & Sawall, LLP

(57) ABSTRACT

A detector for determining the volume and volumetric changes of respiratory gases in a closed circuit anaesthesia circuit having a bellows ventilator. The device includes a first sensor positioned with respect to the bellows for detecting and indicating when the bellows assumes a given expanded position in a bellows housing indicative of the given volume of respiratory gas in the circuit. A second sensor detects and indicates when the bellows assumes an expanded position indicative of the greater amount of expansion than that corresponding to the given expanded position. During respiratory cycles of the patient, indications from the first sensor in the absence of indications from the second sensor indicates that the volume of gas in the closed circuit anaesthesia circuit is not changing, but is remaining at that corresponding to the given expanded position of the bellows. Indications from both the first sensor and the second sensor indicates that the degree of expansion of the bellows is greater than that corresponding to the given expanded position and hence the volume of gas in the closed circuit anaesthesia circuit has increased. The absence of indications from both the first and second sensors indicates that the degree of expansion of the bellows is less than that corresponding to the given expanded position and that the volume of gas in the closed circuit anaesthesia circuit has decreased.

27 Claims, 3 Drawing Sheets

DEVICE AND METHOD FOR DETERMINING GAS VOLUME AND VOLUMETRIC CHANGES IN A VENTILATOR

BACKGROUND OF THE INVENTION

The present invention relates to a device by which the volume of respiratory gas in an anaesthesia circuit and changes in such gas volume can be accurately, rapidly, and easily determined. The invention is particularly suited for use in an anaesthesia circuit operating in the closed circuit mode to enable an appropriate control apparatus or an attending anesthesiologist or other medical personnel to establish and maintain the gas volume in the circuit to a desired, generally constant, level.

Apparatus for administering an inhaled anaesthetic agent to a patient typically includes an anaesthesia machine in which the anaesthetic agent is entrained in a flow of carrier gas. The carrier gas is usually a mixture of oxygen and nitrous oxide or air. The carrier gas and entrained anaesthetic agent from the anaesthesia machine are provided to an anaesthesia circuit for delivery to a patient in the course of his/her respiration. The anaesthesia circuit is typically operated in one of two modes: a semi-closed mode or a closed circuit mode. In the semi-closed mode, the amount of gas supplied to the circuit from the anaesthesia machine exceeds that taken up by the patient. The excess gas is discharged from the circuit to a scavenging system through a pressure limiting, or "pop off", valve during the exhalation phase of the patient's breathing.

In the closed circuit mode the respiratory gases in the circuit, including gas exhaled by the patient, are not discharged from the circuit but are retained in the closed circuit for recirculation to and from the patient. To absorb the carbon dioxide contained in the respiratory gases exhaled by the patient, a $CO_2$ absorber employing a suitable absorbent, such as soda lime, is provided in the circuit.

In a closed circuit anaesthesia system, once the patient is brought to near equilibrium with the respiratory gas contained in the anaesthesia circuit, the amount of gas supplied to the circuit is only the small amount necessary to provide the patient minute oxygen consumption plus some minimal level of anaesthetic agent.

Closed circuit anaesthesia systems have numerous advantages over semi-closed or open systems. These include decreased use of carrier gas and anaesthetic agent. This results in decreased costs from the lessened consumption of the carrier gas and the anaesthesia agent. The amount of environmental pollution is lessened because of the closed nature of the circuit. In a closed circuit system, the patient minute oxygen consumption can be rather precisely determined since, with the circuit at equilibrium, the amount of oxygen supplied to the closed circuit in the gas flow from the anaesthesia machine will be the same as that which the patient is consuming.

However, closed circuit anaesthesia circuits have not achieved as wide spread usage as their advantages would warrant. This is due, in considerable measure, to the fact that a closed anaesthesia circuit requires continuous monitoring of the volume and composition of the respiratory gas in the circuit and careful maintenance of those characteristics by controlling the amount and composition of the gas flow supplied to the closed circuit.

The gas volume in a closed circuit anaesthesia circuit is evident from a bellows assembly of the attached ventilator. The bellows assembly includes an expandable, pleated bellows, formed of rubber or other flexible material. The bellows is connected in the closed circuit for receiving and discharging gas respired by the patient. The bellows is contained in a surrounding rigid housing, typically formed of clear plastic. To cause or assist the patient to inhale respiratory gas, a separate, driving gas is supplied to the housing to compress the bellows and deliver respiratory gas in the closed circuit to the patient. As the patient exhales, the driving gas is allowed to exit the housing so that the bellows may expand to receive respiratory gas exhaled by the patient. The process is then repeated for the next breathing cycle of the patient. The bellows is typically compressed downwardly during inhalation and expands upwardly during exhalation, and the housing surrounding the bellows is cylindrical in nature, with a vertical volumetric scale.

The anesthesiologist, or others, using an anaesthesia system in a closed circuit mode, adjusts the gas volume in a closed circuit system so that the bellows rises, with the patient's exhalation, to an intermediate position on the vertical scale of the housing. Changes in the gas volume in the closed circuit are determined by observing changes in the position of the bellows in the housing at the end of successive breathing cycles of the patient. For instance, if the bellows is gradually rising higher and higher with each exhalation of the patient, the volume of gas in the closed circuit is increasing. The anesthesiologist must slightly decrease the gas supply of one or more of the gases supplied to the closed circuit to restore and maintain the desired constant volume in the circuit. If, on the other hand, the bellows is gradually returning to a lower and lower position in the housing with each exhalation, the anesthesiologist will need to add gas from one or more of the gas supplies to the closed circuit. When the desired goal of maintaining the volume of gas in the closed circuit at a constant level is being achieved, the bellows will return with each exhalation to the same intermediate position in the housing.

The desired composition for the respiratory gases in the closed circuit is determined by measuring the oxygen concentration in the closed circuit, typically the inspired oxygen concentration ($FiO_2$), and the amount and composition of the gas supplied to the circuit is adjusted to maintain the oxygen concentration at a desired level.

The need for continuous monitoring of gas volume and composition and careful maintenance of these characteristics places a corresponding burden on the anesthesiologist attending a patient to observe the magnitude of the gas volume, the nature of changes therein, and composition of the respiratory gas in the closed anaesthesia circuit and to properly operate the appropriate gas supply values in response to such observations. These requirements are in addition to other demands on the anesthesiologist, for example, to monitor the physiological condition of the patient during a surgical or other medical procedure.

The foregoing burden has caused anesthesiologists to employ other modes of operation instead of closed circuit anaesthesia circuits, in spite of the advantages of the latter.

BRIEF SUMMARY OF THE INVENTION

It is, therefore, the object of the present invention to provide a device by which the magnitude and changes of the volume of respiratory gas in an anaesthesia circuit can be accurately, rapidly, and easily determined, thereby to overcome the above noted deterrents to the use of an anaesthesia circuit in the closed circuit mode.

The device of the present invention is simple, sturdy, and economical in construction and operation and lends itself to use with control apparatus by which changes in the amount and composition of gas supplied to the closed circuit may be automatically effected.

To achieve the foregoing objects, the device of the present invention comprises a first sensor positioned with respect to the bellows of the anaesthesia circuit for detecting and indicating when the bellows assumes a given expanded position in the housing, the given position being indicative of given volume of gas in the anaesthesia circuit. The sensor may comprise a light source and photo detector positioned diametrically opposite each other on the housing for the bellows. The bellows, when in the given position, breaks the light beam between the light source and the photo-detector to provide an indication from the latter that the bellows has attained the given position and that a given volume of gas exists in the anaesthesia circuit.

A second sensor is positioned with respect to the bellows for detecting and indicating when the bellows assumes an expanded position which is beyond the given expanded position in the housing in the direction of expansion of the bellows. The second sensor may also be formed of a light source and a photo-detector.

During successive respiratory cycles of the patient, repetitive indications from the first sensor, in the absence indications from the second sensor, indicates that a given volume of gas in the anaesthesia circuit for the patient that is not changing. Repetitive indications from both the first sensor and the second sensor indicate that the volume of gas in the anaesthesia circuit has increased and the absence of indications from both said first sensor and said second sensor indicate that the volume of gas in the anaesthesia circuit has decreased.

The present invention is also directed to a bellows assembly having such a device for determining gas volumes and changes therein in an anaesthesia circuit.

The present invention is also directed to a method for determining gas volumes and gas volume changes in an anaesthesia circuit.

The present invention will be further understood and appreciated by reference to the following detailed description and accompanying drawing.

DETAILED DESCRIPTION OF THE INVENTION

Figure 1:
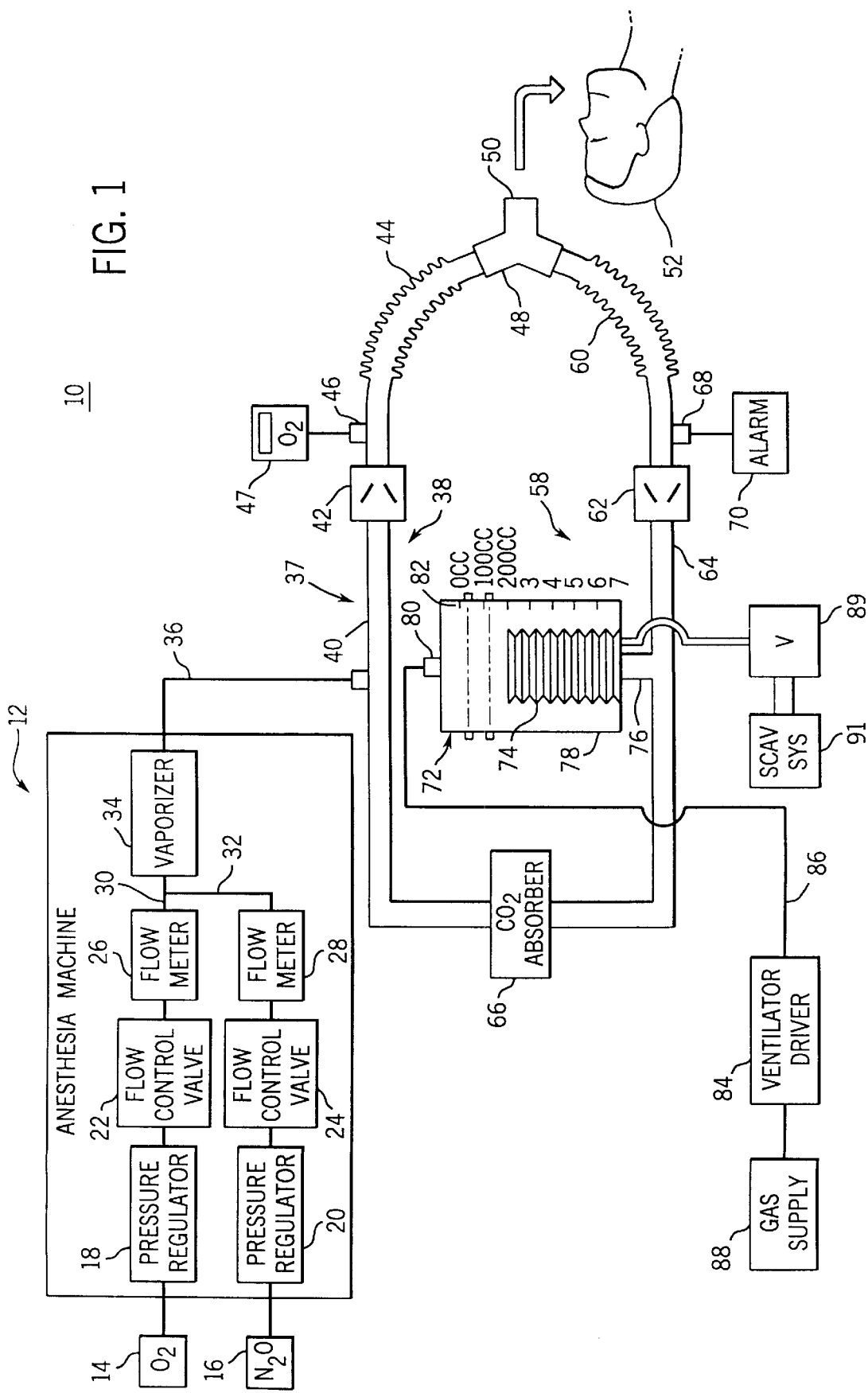
FIG. 1 shows, in generally schematic form, an anaesthesia apparatus incorporating an anaesthesia ventilator circuit.

FIG. 1 shows anaesthesia apparatus 10 having anaesthesia machine 12. Anaesthesia machine 12 is coupled to a plurality of sources of breathable gases, such as oxygen ($O_2$), and nitrous oxide ($N_2O$) and/or air. FIG. 1 shows anaesthesia machine 12 coupled to oxygen supply 14 and nitrous oxide supply 16. Anaesthesia machine 12 may include pressure regulators 18, 20; gas flow control valves 22, 24; and flow meters 26, 28 in conduits 30 and 32, respectively coupled to oxygen supply 14 and nitrous oxide supply 16. Conduits 30 and 32 are joined together upstream of vaporizer 34 containing an anaesthetic agent. The breathable gases from conduits 30 and 32, having the anaesthesia agent entrained therein in vaporizer 34, are discharged in gas supply conduit 36 to anaesthesia circuit 37.

Anaesthesia circuit 37 includes an inhalation limb 38 comprised of conduit 40, inhalation check valve 42, and inhalation hose 44. Inhalation hose 44 is connected to the inlet of Y-piece connector 48. Opening 50 of Y-piece connector 48 supplies respiratory gases to patient 52 during inhalation and receives respiratory gases from the patient during exhalation, typically through an endotracheal tube or laryngeal mask airway.

Anaesthesia circuit 37 also includes an exhalation limb 58. Exhalation limb 58 is comprised of exhalation hose 60, connected to the output of Y-piece connector 48, exhalation check valve 62, and conduit 64. Conduit 64 is connected to the inlet of carbon dioxide ($CO_2$) absorber 66, the outlet of which is connected to conduit 40 in inhalation limb 38 to complete the anaesthesia circuit. $CO_2$ absorber 66 may contain soda lime or other suitable $CO_2$ absorbent. A pressure sensor 68 may be connected in anaesthesia circuit 37, as at the patient side of exhalation check valve 62, to detect excessively high or low pressures resulting from disconnection or misconnection of the various elements, conduits, hoses, and connectors of the anaesthesia circuit. Sensor 68 operates alarm 70. Oxygen sensor 46 may be coupled in inhalation limb 38 at the outlet side of inhalation check valve 42 to measure the inspired oxygen concentration and provide same to readout 47. Anaesthesia circuit 37 may also include other desired elements, not shown, such as a bacteria filter or a humidifier.

Bellows assembly 72 is connected in anaesthesia circuit 37 downstream of exhalation check valve 62, as for example, to conduit 64. Bellows assembly 72 includes expandable, pleated bellows 74. Bellows 74 is connected to conduit 64 by pipe 76. Bellows 74 is contained in housing 78, which is sealed, except for the opening at connection 80. In typical anaesthesia apparatus currently in use, bellows 74 expands upwardly and contracts downwardly in housing 78. Housing 78 has vertical scale 82. Due to the fact that, in a semi-closed mode of operation, the scale is conventionally used to determine the tidal volume of respiratory gas delivered to the patient, the scale is arranged to be indicative of the volume of gas delivered by the bellows upon contraction, i.e. the zero mark (0 cc) is at the top of the scale and lower marks (200 cc, 300 cc, etc.) show the volume by which the bellows has been compressed.

Bellows assembly 72 is operated by ventilator driver 84 which is coupled to connector 80 of housing 78 by gas line 86. Ventilator driver 84 supplies driving gas from gas source 88 to bellows housing 78 via gas line 86 and removes gas from housing 78. Other types of ventilator drivers may be employed, if desired.

A pressure relief, or pop off, valve 89 and associated scavenging system 91 is also provided in anaesthesia circuit 37.

The startup procedures for anaesthesia circuit 37 are as follows. The circuit is flushed and filled with respiratory gas from gas supply conduit 36. Anaesthesia circuit 37 is initially operated in the semi-closed mode until operation in the closed mode can be achieved. Ventilator driver 84 is operated to supply driving gas to housing 78 of bellows apparatus 72 via gas line 86. The gas so supplied compresses bellows 74 downwardly, forcing the respiratory gases in the bellows and in the downstream portions of anaesthesia circuit 37, through conduit 64, carbon dioxide absorber 66, conduit 40, inhalation check valve 42, inhalation hose 44, Y-piece connector 48 to patient 52. The volume of respiratory gases delivered to patient 52 is determined by the amount of driving gas supplied to housing 78. To allow removal of the respiratory gases exhaled by the patient during exhalation, the driving gas in housing 78 of bellows assembly 72 is allowed to exit the housing, permitting bellows 74 to expand upwardly to receive the exhaled gases as the patient breathes out. The exhaled gases are provided to bellows 74 via exhalation hose 60, exhalation check valve 62 and conduit 64.

On the next breath for patient 52, bellows 74 is again compressed, to deliver its contents to conduit 64. The $CO_2$ in the respiratory gas previously exhaled by the patient and contained in bellows 74 is removed by $CO_2$ absorber 66 and the respiratory gas passes to inhalation limb 38 for delivery to patient 52. The respiratory gases subsequently exhaled by the patient are again received in exhalation limb 58 and bellows 74.

In the event excess gas is present in anaesthesia circuit 37, at the end of exhalation, bellows 74 will be full and the excess gas will exit through pop off valve 89 into scavenging system 91, as operation is in the semi-closed mode. In the event a lower amount of gas is present in the circuit, the bellows will not rise to the desired level. Respiratory gas is added to the circuit to bring the position of the bellows at the end of exhalation up to a desired mark on housing 78, for example the 100 cc mark, which is used as an indicator that the desired volume of gas is present in the anaesthesia circuit.

After the initial filling adjustment of anaesthesia circuit 37, the volume of respiration gases in the circuit then remains generally constant, the supply of additional gas to the circuit being in the amounts required to restore quantities of gas consumed by patient 52 and lost through leakage. The operation of the anaesthesia circuit is that of the closed circuit mode. The composition of the gas so supplied is altered to maintain the desired oxygen concentration in the circuit.

Figure 2:
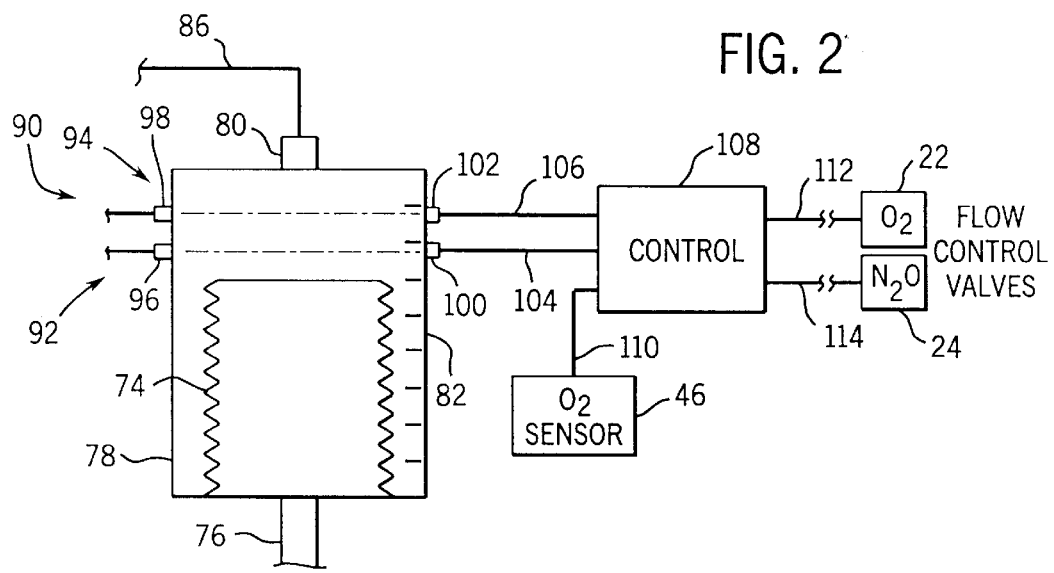
FIG. 2 is a view of one embodiment of the device of the present invention for determining changes in gas volume in the anaesthesia circuit.

The device 90 of the present invention for determining volumetric amounts and changes in the gas volume in anaesthesia circuit 37 operating in the closed circuit mode is shown in detail in FIG. 2. Device 90 includes a pair of detectors, lower detector 92 and upper detector 94, for determining the height attained by bellows 74 in housing 78 during the expiration phase of the patient's breathing. Detectors 92 and 94 may, for example, comprise light operated detectors, having lower and upper light sources 96 and 98 mounted on one side of housing 78 to pass lower and upper beams of light through housing 78. Light sensors 100 and 102 are mounted on the opposite side of housing 78 to receive the lower and upper light beams from light sources 96 and 98, respectively. The light produced by light sources 96 and 98 can be visible or outside the visible portion of the electromagnetic spectrum, for example, infrared.

Light sensors 100 and 102 provide outputs in conductors 104 and 106, respectively, indicating the operative state of detectors 92 and 94. Conductors 104 and 106 may be connected to control 108. Control 108 may also receive an input in conductor 110 from oxygen sensor 46 connected in inspiration limb 38 of anaesthesia circuit 37. Control 108 provides an output in conductors 112 and 114 to control valves 22 and 24 of anaesthesia machine 12 regulating the flow of oxygen and nitrous oxide gases, respectively.

Lower detector 92 is positioned on housing 78 for bellows 74 so that when bellows 74 is in a given, expanded position in housing 78, corresponding to a given volume of gas in the anaesthesia circuit, the lower light beam from light source 96 will be broken by the upper end of the bellows.

Upper detector 94 is positioned above lower detector 92 so that the light beam from light source 98 will be broken by the upper end of bellows 74 when bellows 74 assumes an expanded position which is beyond the given expanded position in the upward direction of movement of bellows 74. The amount by which upper detector 94 is displaced above lower detector 92 is selected in accordance with a desired increment of upward movement of bellows 74, and hence a given incremental increase in the volume of the bellows, in accordance with the accuracy of volumetric change determination desired in device 90, and in a manner to provide a desired degree of stability in determining the accuracy of the volumetric changes.

Figure 3:
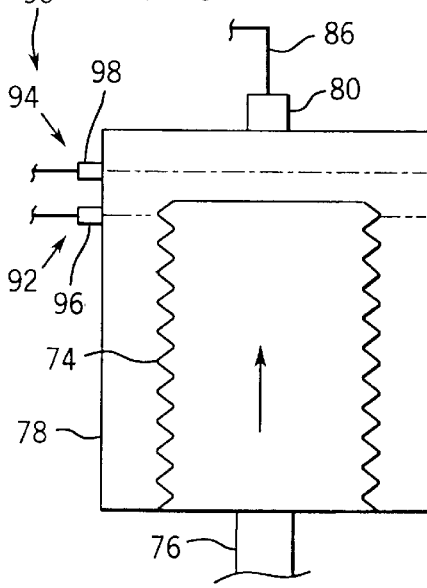
FIGS. 3, 4 and 5 are views similar to FIG. 2 showing operation of the device of the present invention.

The operation of device 90 of the present invention is as follows. During exhalation by the patient, bellows 74 will move in an upwardly direction. Since the respiratory gas is removed from the lungs of the patient upon exhalation, the position of bellows 74 in housing 78 will be an indication of the volume of gas in closed circuit anaesthesia circuit 37. During the initial startup of anaesthesia circuit 37, described above, with a desired volume of gas supplied to the circuit from anaesthesia machine 12, when the patient exhales, bellows 74 will be expanded to a condition in which the upper portion of bellows 74 lies at a given, expanded position within the range of vertical scale 82. For example, upon exhalation, the upper end of bellows 74 may be aligned with the 100 cc, 200 cc, or 300 cc mark etc. of scale 82 depending on the desired volume of gas in the circuit. The selection mark serves as a reference point for volumetric determination. As shown in FIG. 3, lower detector 92 and upper detector 94 are positioned with respect to bellows 74 such that the upper end of bellows 74 interrupts the light beam provided by lower light source 96 but not the light beam provided by upper light source 98 when bellows 74 attains the given, expanded position. For this purpose, lower and upper detectors 92 and 94 may be adjustably positioned, as a unit, on bellows housing 78.

During successive respiratory cycles of the patient, if the volume of respiratory gases in anaesthesia circuit 37 is not changing, during the exhalation phase of each respiratory cycle, the upper end of bellows 74 will return upwardly each time to the same given, expanded position, in which the upper end of the bellows breaks the light beam from lower light source 96 but does not break the light beam from upper light source 98. The fact that the lower light beam is broken but the upper beam is not broken is detected by light sensors 100 and 102, respectively, and the signal state of the light sensors in conductors 104 and 106 is an indication that the volume of gas in anaesthesia circuit 37 operating in the closed circuit mode is at the desired level and is not changing.

Figure 4:
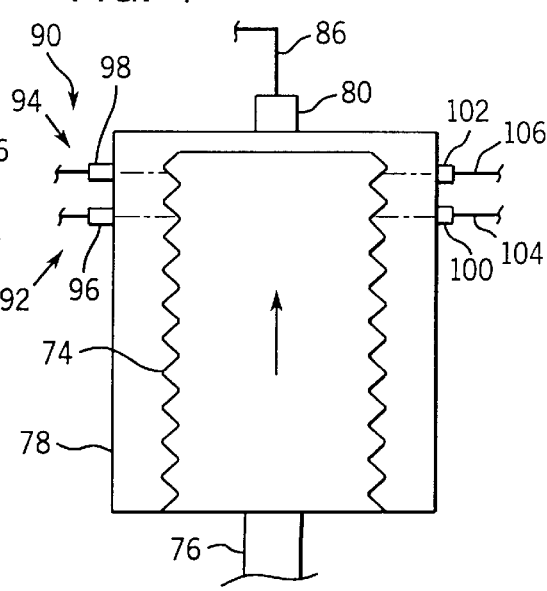

Should the volume of respiratory gases in closed circuit anaesthesia circuit 37 increase from the desired level, bellows 74 will expand upwardly to a greater extent, due to the increased gas volume in the circuit. As a result of the greater upward expansion of bellows 74, the upper portion of the bellows will now break both the lower and upper beams of light passing through housing 78 from lower and upper light sources 96 and 98 to light sensors 100 and 102, respectively. See FIG. 4. The interruption of both the upper and lower light beams will be detected by light sensors 100 and 102, and the corresponding output state of both the sensors in conductors 104 and 106 comprises an indication that the volume of gases in anaesthesia circuit 37 has increased.

Figure 5:
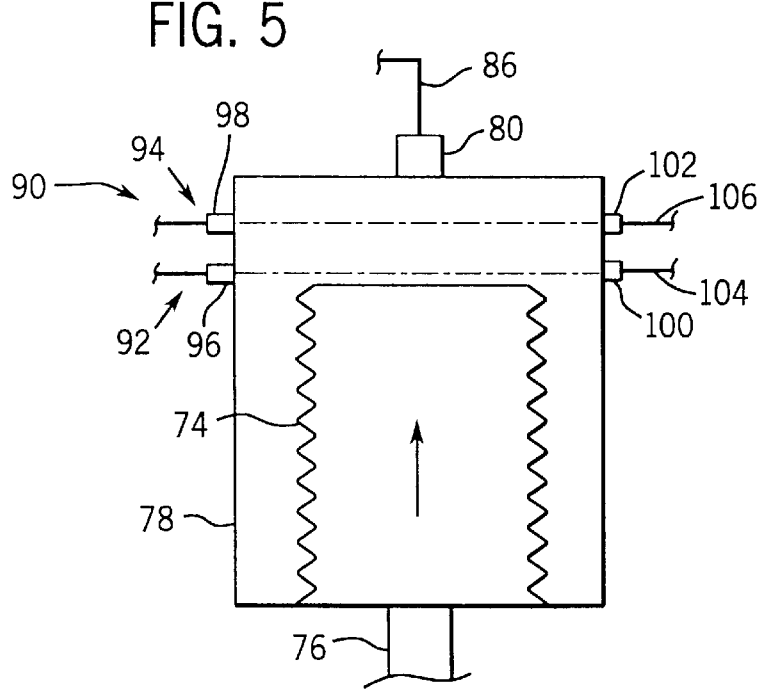

Conversely, if the volume of respiratory gases in closed circuit anaesthesia circuit 37 decreases from the desired level, the amount by which bellows 74 expands upwardly in housing 78 will decrease, due to the decreased gas volume in the circuit. As shown in FIG. 5, neither the upper light beam nor the lower light beam will be broken by the upper portions of bellows 74 in this circumstance. Lower and upper light sensors 100 and 102 will provide corresponding outputs in conductors 104 and 106 which form an indication that the volume of respiratory gases in anaesthesia circuit 37 has decreased.

In the foregoing manner, the output states of upper and lower light sensors 100 and 102 provide a simple, reliable, and straightforward indication of whether the gas volume in anaesthesia circuit 37 operating in the closed circuit mode is at the desired level, has increased, or has decreased.

Figure 6:
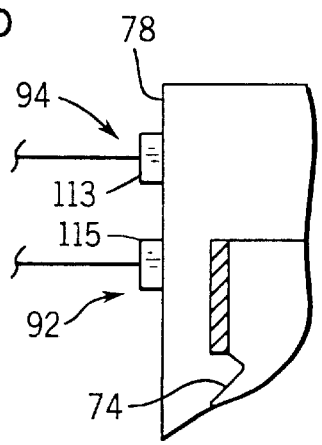
FIGS. 6 and 7 are fragmentary views showing modifications to the device of the present invention.
Figure 7:
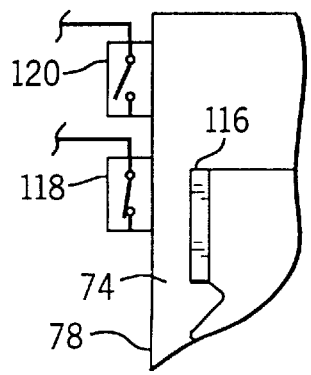

While optical detectors 92 and 94 are shown in FIG. 2, it will be appreciated that other types of detectors may be employed in the device of the present invention. For example, FIG. 6 schematically shows an electrical detector in the form of a capacitive detector means and FIG. 7 shows a magnetic detector in the form of magnet 116 mounted on the upper portion of bellows 74 and magnetically operable reed switches 118, 120 mounted on housing 78. In the event a different type of ventilator driver 84 is employed for bellows 74, other types of detectors, such as mechanical switches, may be employed.

Also, while FIG. 2 shows the light sources and light sensors mounted on opposite sides of bellows 74, it will be appreciated that the light sources and light sensors may be mounted on the same side of bellows 74 and a light reflecting mirror positioned beyond the other side of bellows 74. If desired, the mirror can be mounted on the upper portion of bellows 74 in the same manner as the electrical or magnetic arrangements shown in FIGS. 6 and 7. Or, a light source could be mounted on bellows 74 for use with appropriate sensors on housing 78.

As noted above, the sensor elements of device 90, such as light sensors 100 and 102, may be connected to control 108 that, in turn, is connected to the gas flow controlling valves 22 and 24 of anaesthesia machine 12. Control 108 is also connected, via conductor 110, to oxygen sensor 46 connected in inspiration limb 38 of anaesthesia circuit 37. Oxygen sensor 46 measures the inspired oxygen concentration ($FiO_2$) in anaesthesia circuit 37.

Control 108 may carry out automatic control of the volume and composition of respiratory gas in anaesthesia circuit 37 by appropriate operation of valves 22 and 24 in accordance with the inputs received from conductors 104, 106, and 110. This operation may be carried out in accordance with the following logic table which shows circuit conditions and operation as $FiO_2$ varies with respect to a desired level as set by an anesthesiologist or other operator.

|  | Circuit Volume Increasing | Circuit Volume Steady | Circuit Volume Decreasing |
| --- | --- | --- | --- |
| $FiO_2$ Increasing | Decrease $O_2$ Flow | Decrease $O_2$ Flow and Increase $N_2O$ Flow | Increase $N_2O$ Flow |
| $FiO_2$ Steady | Decrease $O_2$ Flow and $N_2O$ Flow | Nothing | Increase $O_2$ Flow and $N_2O$ Flow |
| $FiO_2$ Decreasing | Decrease $N_2O$ Flow | Increase $O_2$ Flow and Decrease $N_2O$ Flow | Increase $O_2$ Flow |

While the anaesthesia apparatus has been described as having detectors 92 and 94 connected to control 108 for automatic operation, it will be appreciated that the detector may operate visual or audio indicators to permit manual control of the respiratory gas volume in the anaesthesia circuit by an anesthesiologist, or other medical personnel.

And, although the anaesthesia apparatus has been described as employing oxygen and nitrous oxide, it will also be appreciated that a supply of air may be used in addition to, or in lieu of, the nitrous oxide. Or, the apparatus may be operated solely with oxygen.

Thus, while specific embodiments of the device of the present invention have been described above, along with a number of modifications thereof, other modifications, alterations, and changes may be made to the device without departing from the present invention. It is intended to cover all such modifications, alterations, and changes within the scope of the following claims.

What is claimed is:

1. A ventilator for ventilating a subject with breathing gas, said ventilator comprising:

a breathing circuit containing breathing gas for the subject, a portion of the breathing gas being respired by the subject, said portion being provided from the breathing circuit to the subject during inspiration and received in the breathing circuit from the subject during expiration, said breathing circuit having means for recirculating breathing gas within the circuit for operating the breathing circuit in a closed circuit mode;

a bellows assembly for said breathing circuit, said bellows assembly comprising:

a housing;

a bellows positioned in said housing and coupled in fluid communication with said breathing circuit, said bellows receiving a quantity of breathing gas corresponding to the respired breathing gas from said breathing circuit during expiration by the subject to expand the bellows in the housing, said bellows being compressed in said housing to re-circulate breathing gas in said breathing circuit and to supply breathing gas comprising the respired portion of the breathing gas to the subject during inspiration by the subject, said bellows being movable in said housing during the expansion and compression in a path of movement extending between spaced end points in said housing, said bellows being movable in a first direction along the path of movement upon compression and returning in a second direction, opposite to the first direction, upon expansion, said bellows repetitiously assuming an expanded position in said housing in accordance with the volume of the respired breathing gas received in said breathing circuit from the subject and the amount of breathing gas present in the breathing circuit, said expanded position being intermediate said end points;

a ventilation driver coupled to said housing for alternately creating pressure in said housing for compressing said bellows to provide breathing gas in the breathing circuit to the subject as the respired breathing gas portion and relieving pressure in said housing for allowing said bellows to expand to receive a quantity of breathing gas in the breathing circuit corresponding to the respired portion of the breathing gas; and sensor apparatus for determining that the volume of the respired portion of the breathing gas corresponds to a desired volume and for determining whether the amount of breathing gas in the breathing circuit has increased or decreased with respect to a given amount of breathing gas, said sensor comprising:

a first sensor positioned along the path of movement of said bellows at a first point intermediate said end points which corresponds to the expanded position of said bellows when the desired volume of gas is being respired by the subject with the given amount of breathing gas in the breathing circuit, said first sensor detecting and providing an indication when said bellows is present in said housing at said first point; and a second sensor positioned along the path of movement of said bellows at a second point intermediate said end points, said second point being incrementally spaced from said first point in said second direction of movement of said bellows, said second sensor detecting and providing an indication when said bellows is present in said housing at said second point;

said first and second sensors being positioned along the path of movement of said bellows such that both said first and second sensors detect and provide indications when said bellows is at said second point, an indication from said first sensor in the absence of an indication from said second sensor indicating that the volume of the respired portion of the breathing gas corresponds to the desired volume and the given amount of breathing gas is present in the breathing circuit, repetitious indications from said first sensor in the absence of indications from said second sensor indicating that the amount of breathing gas in the breathing circuit is generally not changing, indications from both said first sensor and said second sensor indicating that the amount of breathing gas in the breathing circuit is greater than the given amount, and the absence of indications from both said first sensor and said second sensor indicating that the amount of breathing gas in the breathing circuit is less than the given amount.

2. A ventilator according to claim 1 wherein said first and second sensors are adjustably positioned along the path of movement for the bellows.

3. A ventilator according to claim 1 further defined as one for maintaining the amount of breathing gas in a closed breathing circuit, said ventilator further including control means coupled to said first and second sensors, said control means being coupled to gas supply means for the breathing circuit, said control means being responsive to the indications of said sensors for operating the gas supply means to maintain the amount of breathing gas in the closed breathing circuit.

4. A ventilator according to claim 3 further defined as one for providing an anaesthetic agent to the subject and wherein said gas supply means includes a source of anaesthetic agent.

5. A ventilator according to claim 3 wherein said gas supply means includes a source of oxygen gas, wherein the circuit further includes means for measuring and indicating an oxygen concentration in the breathing circuit, and wherein said control means is couplable to the oxygen concentration measuring and indicating means and is responsive to the indication of said means for operating the gas supply means.

6. A ventilator according to claim 5 further defined as one for providing an anaesthetic agent to the subject and wherein said gas supply means includes a source of anaesthetic agent.

7. A ventilator according to claim 1 further defined as one for providing an anaesthetic agent to the subject and as including a source of anaesthetic agent coupled to said breathing circuit.

8. A ventilator according to claim 1 wherein said first and second sensors are incrementally spaced from each other along a direction generally parallel to the path of movement of said bellows.

9. A ventilator according to claim 8 wherein said first and second sensors are incrementally spaced from each other by an amount selected in accordance with the accuracy and stability desired of the sensor apparatus.

10. A ventilator according to claim 1 wherein said bellows is positioned in said housing to move upwardly upon expansion and downwardly upon compression and wherein said first and second sensors are oriented with respect to each other such that the first sensor comprises a lower sensor and said second sensor comprises an upper sensor located above said first, lower sensor in the second direction of movement along the path of movement of said bellows.

11. A ventilator according to claim 1 wherein at least one of the said sensors comprises a light operated sensor.

12. A ventilator according to claim 11 wherein said at least one sensor comprises a light source emitting a light beam and a light detector for receiving light, the position of the bellows determining whether the light beam is received by said light detector.

13. A ventilator according to claim 11 wherein said at least one sensor comprise a light source emitting a light beam and a light detector for receiving light, the light beam being broken by said bellows by movement along the path of movement.

14. A ventilator according to claim 12 wherein said at least one sensor includes a mirror for reflecting the light beam.

15. A ventilator according to claim 1 wherein at least one of said sensors comprises magnetically operated sensor means.

16. A ventilator according to claim 1 wherein at least one of said sensors comprise electrically operated sensor means.

17. A ventilator according to claim 16 wherein at least one of said sensors comprises capacitively operated sensor means.

18. A ventilator according to claim 1 wherein at least one of said sensors comprises mechanically operated sensor means.

19. A method for determining that a volume of breathing gas respired by a subject and provided by a breathing circuit corresponds to a desired volume and for determining whether the amount of breathing gas in the breathing circuit has increased or decreased with respect to a given amount of breathing gas, the breathing circuit providing a portion of the breathing gas in the breathing circuit to a subject as respired breathing gas during inspiration by the subject and receiving the respired portion of the breathing gas from the subject during expiration by the subject, the breathing circuit re-circulating breathing gas in the breathing circuit to operate the breathing circuit in a closed circuit mode, the breathing circuit including a bellows assembly having a housing and a bellows positioned in the housing and coupled in fluid communication with the breathing circuit, the bellows receiving a portion of breathing gas corresponding to the respired portion of the breathing gas from the breathing circuit during expiration by the subject to expand the bellows in the housing, the bellows being compressed in said housing to re-circulate breathing gas in the breathing circuit and to supply breathing gas comprising the respired portion of the breathing gas to the subject during inspiration by the subject, the bellows being movable in the housing in a path of movement extending between spaced end points in the housing, the bellows moving in a first direction along the path of movement upon compression and returning in a second direction, opposite to the first direction, on expansion, the bellows assuming an expanded position in the housing in accordance with the volume of the respired portion of the breathing gas received in the breathing circuit from the subject and the amount of breathing gas present in the breathing circuit, the expanded position being intermediate said end points, the breathing circuit having a first sensor positioned along the path of movement of the bellows at a first point intermediate the end points which corresponds to the expanded position of the bellows when the desired volume of gas is being respired the subject with a given amount of breathing gas in the breathing circuit, and the breathing circuit having a second sensor positioned along the path of movement of said bellows at a second point intermediate said end points, said second point being incrementally spaced from said first point in said second direction of movement of said bellows, said method comprising the steps of:

allowing the bellows to expand in the housing along the second direction of movement responsive to receiving the respired breathing gas portion in the breathing circuit from the subject;

detecting whether, as a result of the expansion of the bellows when the respired breathing gas portion is received, no sensor is operated, only the first sensor is operated, or both the first and second sensors are operated;

determining that the desired volume of gas is being respired and the amount of gas in the breathing circuit is the given amount when only the first sensor is operated, determining that the amount of breathing gas in the breathing circuit has increased over the given amount when both the first and second sensors are operated, and determining that the amount of breathing gas in the breathing circuit has decreased from the given amount when neither the first and second sensors are operated; and compressing the bellows along the first direction of movement to recirculate breathing gases in the breathing circuit and supply respired breathing gas to the subject.

20. The method according to claim 19 wherein the expansion and compression of the bellows is alternately carried out, wherein the detecting step is carried out repetitiously, and wherein the determining step is further defined as determining from a change from first sensor operation to no sensors being operated that the amount of breathing gas in the breathing circuit has decreased, and determining from a change from first sensor operation to both sensors being operated that the amount of breathing gas in the breathing circuit has increased.

21. The method according to claim 20 wherein the breathing circuit has a gas supply means and wherein the method further includes the step of controlling the supply of gas to the breathing circuit in accordance with the determination made in said determining step.

22. The method according to claim 21 wherein the breathing circuit includes a source of oxygen gas and wherein said method includes the step of measuring the oxygen concentration in the breathing circuit and controlling the supply of oxygen gas to the breathing circuit in accordance with said measurement.

23. The method according to claim 22 further defined as controlling the supply of gas to provide an anaesthetic agent to the subject.

24. The method according to claim 19 wherein the breathing circuit has a gas supply means and wherein the method further includes the step of controlling the supply of gas to the breathing circuit in accordance with the determination made in said determining step.

25. The method according to claim 24 further defined as controlling the supply of gas to provide an anaesthetic agent to the subject.

26. The method according to claim 19 wherein the method includes the step of displacing the first and second sensors from each other along a direction generally parallel to the path of movement of the bellows.

27. The method according to claim 26 wherein the step of incrementally spacing the first and second sensors is further defined as incrementally pacing the sensors from each other by an amount selected in accordance with the accuracy and stability desired in the determination step.

* * * * *